(12) United States Patent
Lu et al.

(10) Patent No.: US 9,512,001 B2
(45) Date of Patent: Dec. 6, 2016

(54) FLUORESCENT MAGNETIC NANOPARTICLES AND PROCESS OF PREPARATION

(75) Inventors: Huachang Lu, Beijing (CN); Guangshun Yi, Beijing (CN); Depu Chen, Beijing (CN); Lianghong Guo, Beijing (CN); Jing Cheng, Beijing (CN)

(73) Assignees: CAPITALBIO CORPORATION, Beijing (CN); TSINGHUA UNIVERSITY, Beijing (CN)

( * ) Notice: Subject to any disclaimer, the term of this patent is extended or adjusted under 35 U.S.C. 154(b) by 450 days.

(21) Appl. No.: 12/970,688

(22) Filed: Dec. 16, 2010

(65) Prior Publication Data

US 2011/0177339 A1 Jul. 21, 2011

Related U.S. Application Data

(63) Continuation of application No. 10/567,535, filed as application No. PCT/CN03/00666 on Aug. 13, 2003, now Pat. No. 7,875,466.

(30) Foreign Application Priority Data

Aug. 8, 2003 (CN) .............. 2003 1 153215

(51) Int. Cl.
*G01N 33/543* (2006.01)
*B82Y 15/00* (2011.01)
*G01N 33/58* (2006.01)

(52) U.S. Cl.
CPC .......... *B82Y 15/00* (2013.01); *G01N 33/54326* (2013.01); *G01N 33/588* (2013.01); *Y10T 428/2991* (2015.01)

(58) Field of Classification Search
CPC ............ A61K 49/0065; A61K 49/0058; A61K 49/0067; A61K 49/0423; A61K 49/1875; A61K 9/5115; G01N 33/54326; G01N 21/64
USPC ........................................................ 436/526
See application file for complete search history.

(56) References Cited

U.S. PATENT DOCUMENTS 4,157,323 A * 6/1979 Yen et al. ................ 522/84
4,554,088 A 11/1985 Whitehead et al.
(Continued)

FOREIGN PATENT DOCUMENTS

CN 1347958 A 5/2002
CN 1376759 A 10/2002
(Continued)

OTHER PUBLICATIONS

Hatanaka et al., *Journal of Applied Physics* (2003) 93(10):7569-7570.
(Continued)

*Primary Examiner* — Mark Shibuya
*Assistant Examiner* — Pensee Do
(74) *Attorney, Agent, or Firm* — Morrison & Foerster LLP

(57) ABSTRACT

This invention provides nanometer-sized fluorescent magnetic particles and processes of making them. The nanoparticle has a core particle comprising a magnetic material and a fluorescent material, and the particle size is less than about 1 micrometer. The nanoparticles can be coated with an inorganic or organic layer and can be surface-modified. The nanoparticles can be used in many biological assays.

19 Claims, 5 Drawing Sheets

(56) References Cited

U.S. PATENT DOCUMENTS

| | | | |
|---|---|---|---|
| 4,628,037 A | 12/1986 | Chagnon et al. | |
| 4,672,040 A | 6/1987 | Josephson | |
| 5,759,435 A | 6/1998 | Miyazono et al. | |
| 5,891,361 A | 4/1999 | Kane | |
| 6,013,531 A | 1/2000 | Wang et al. | |
| 6,537,829 B1 | 3/2003 | Zarling et al. | |
| 6,866,838 B1 | 3/2005 | Mondain-Monval et al. | |
| 7,235,228 B2 | 6/2007 | Carpenter et al. | |
| 7,422,703 B2 | 9/2008 | Yi et al. | |
| 2001/0046602 A1* | 11/2001 | Chandler | B03C 1/01 428/403 |
| 2002/0164271 A1 | 11/2002 | Ho | |
| 2003/0207331 A1* | 11/2003 | Wilson et al. | 435/7.1 |
| 2004/0067503 A1* | 4/2004 | Tan et al. | 435/6 |
| 2004/0126902 A1* | 7/2004 | Nishiya et al. | 436/526 |
| 2007/0059705 A1 | 3/2007 | Lu et al. | |

FOREIGN PATENT DOCUMENTS

| | | |
|---|---|---|
| CN | 1157462 C | 7/2004 |
| EP | 1 138 743 A1 | 10/2001 |
| GB | 927492 A | 5/1963 |
| JP | 9-28397 A | 2/1997 |
| JP | 2003-513093 A | 4/2003 |
| WO | WO-91/09141 A1 | 6/1991 |
| WO | WO-01/33223 A1 | 5/2001 |
| WO | WO-01/88540 A1 | 11/2001 |
| WO | WO-04/001414 A1 | 12/2003 |

OTHER PUBLICATIONS

International Search Report for PCT/CN03/000666, mailed on Oct. 10, 2003, 3 pages.
Santra et al., *Anal. Chem.* (2001) 73:4988-4993.
Supplementary European Search Report for EP 03 81 7911, completed Sep. 20, 2006, 2 pages.
Taylor et al., *Anal. Chem.* (2000) 72:1979-1986.
Chen, D. et al. (2002). "Up-converting fluorescent material with nanometer level molybdate substrate and its preparation," Database WPI, Derwent Publications Ltd., London, United Kingdom, Accession No. 2002-567257, Abstract, one page.
Database WPI, accession No. 2002-567257 (2002).

* cited by examiner

 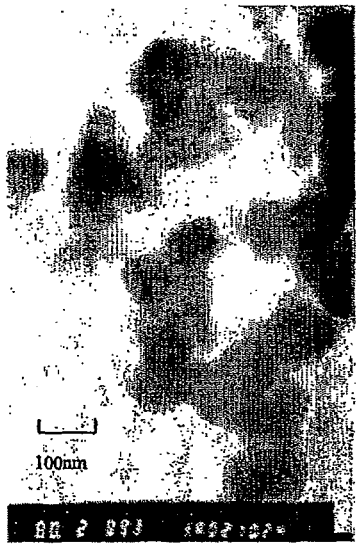 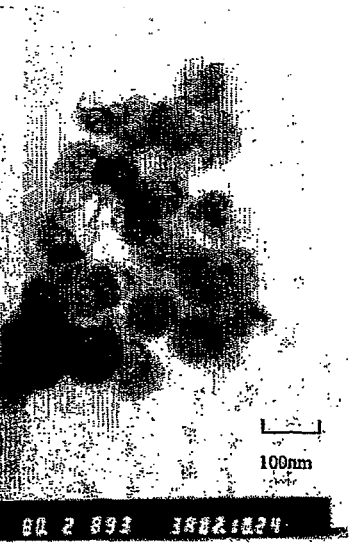
Fig. 4    Fig. 5    Fig. 6
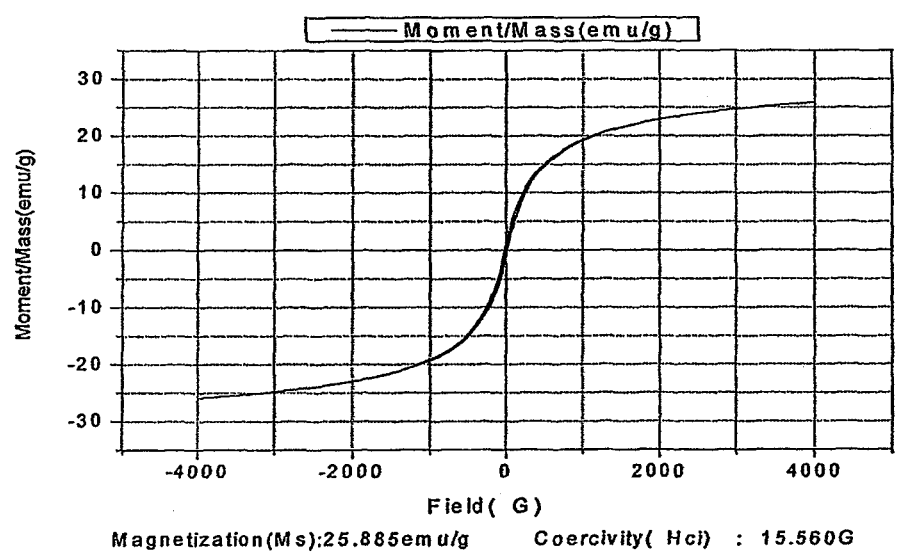
Magnetization(Ms):25.885emu/g    Coercivity(Hci) : 15.560G
Fig. 7

US 9,512,001 B2

FLUORESCENT MAGNETIC NANOPARTICLES AND PROCESS OF PREPARATION

CROSS-REFERENCE TO RELATED APPLICATIONS

This application is a continuation of U.S. application Ser. No. 10/567,535 having an international filing date of Aug. 13, 2003; which is a National Phase filing under 35 U.S.C. §371 of International Application No. PCT/CN2003/000666 having an international filing date of Aug. 13, 2003, which claims priority to Chinese Patent Application No. 031153215.2, filed on Aug. 8, 2003, the entire content of each of which is incorporated herein by reference.

FIELD OF THE INVENTION

This invention relates to hybrid nanoparticles and process of making them. More particularly, the present invention relates to nanometer-sized magnetically responsive fluorescent particles and process of making them.

BACKGROUND OF THE INVENTION

Bio-magnetic particles are surface-modified magnetically responsive microspheres which are widely used in immunoassays, gene engineering, cell separation etc. Roy A. Whitehead and Lee Josephson et al provided a process for the preparation of magnetic particles to which a wide variety of molecules might be coupled. The particles comprised ferromagnetic, superparamagnetic or paramagnetic oxides of iron, cobalt or nickel as a metal oxide core, generally surrounded by an adsorptively or covalently bound sheath or coat bearing organic functionalities to which bio-affinity adsorbents might be covalently coupled. Magnetic particles are useful in biological separations in radioimmunoassay, cell isolation, affinity chromatography, immobilized enzyme systems, nucleic acid hybridization, and other biological systems. See U.S. Pat. No. 4,554,088, U.S. Pat. No. 4,672,040, U.S. Pat. No. 4,628,037.

Fluorescence immunoassay (FIA) is also widely used in biotechnology. There are many fluorescent materials that can be used as fluorescent labels, such as organic fluorescent dyes, quantum dots, down-converting rare-earth phosphor nanoparticles and up-converting phosphor nanoparticles etc.

Wang et al provided a process of preparing magnetically responsive fluorescent polymer particles with sizes ranging from 1 to 100 microns. The fluorescent material was used to determine the number of the particles. These polymer particles comprise polymeric core particles coated evenly with a layer of polymer containing magnetically responsive metal oxide as highly sensitive quantitative reagents for biochemical and immunological studies. The surface of these magnetically responsive polymer particles can be coated further with another layer of functionalized polymer. These magnetically responsive fluorescent polymer particles can be used for passive or covalent coupling of biological material such as antigens, antibodies, enzymes or DNA/RNA hybridization and used as solid phase for various types of immunoassay, DNA/RNA hybridization probes assay, affinity purification, cell separation and other medical, diagnostic, and industrial applications. See U.S. Pat. No. 6,013,531.

Chandler et al provided a process of preparing magnetically-responsive fluorescently-tagged particles. These hybrid microspheres are constructed using fluorescent or luminescent microspheres and magnetic nanoparticles. Reactive moieties on the surface of the resultant particles can be used for attachment of biologically active molecules, thus allowing selective separations and analytical assays to be performed. Distinguishable subsets of microspheres can be constructed based on fluorescent intensities, and separations can be affected based on variable degree of magnetic content. Multiple particles populations thus constructed will find utility in a number of fields, including clinical biological assays See U.S. patent application Ser. No. 09/826,960.

BRIEF SUMMARY OF THE INVENTION

The present invention provides nanometer-sized fluorescent magnetic particles and processes of preparing the nanometer-sized fluorescent magnetic particles. These nanoparticles can be coated with an inorganic or organic layer and can be surface-modified. These nanoparticles can be constructed using fluorescent materials such as fluorescent dyes, fluorescent quantum dots, down-converting rare-earth phosphors, or up-converting phosphors. The magnetic materials for these nanoparticles can be superparamagnetic, paramagnetic, ferromagnetic metal oxide nanoparticles such as $Fe_3O_4$, $\gamma$-$Fe_2O_3$, or other oxides of cobalt, nickel, or manganese. These nanoparticles can be used as both solid phase carrier which can be manipulated by a magnet and fluorescent labels for various types of immunoassay, DNA/RNA hybridization, affinity purification, cell separation and other medical, diagnostic, and industrial applications.

In one aspect, the present invention is directed to a nanoparticle comprising a core particle, wherein the core particle comprises a magnetic material and a fluorescent material, and wherein the nanoparticle has a particle size less than about 1 micrometer.

In another aspect, the present invention is directed to a process of preparing a nanoparticle comprising a magnetic particle coated with a phosphor fluoride, which process comprises: a) dispersing a nanometer-sized magnetic particle and an aqueous fluoride-containing compound in de-ionized water; b) contacting the mixture of step a) with an aqueous solution containing soluble salts of a phosphor host, an absorber/emitter pair, and a rare-earth metal chelator by stirring for a sufficient time to allow formation of a phosphor fluoride precipitate which forms a coating around the magnetic particle; and c) heating the magnetic particle with the phosphor fluoride coating of step b) at a temperature ranging from about 300° C. to about 450° C. for a period of time ranging from about 1 hour to about 10 hours to obtain the phosphor fluoride coated magnetic particle that emits light in the visible wavelength range when excited by long wavelength light.

In another aspect, the present invention is directed to a process of preparing a nanoparticle comprising fluorescent particles and magnetic particles coated with silica, which process comprises: a) dispersing nanometer-sized magnetic particles and nanometer-sized fluorescent particles in an alcohol; b) adding de-ionized water and ammonia having a concentration of about 28% (w/w) to the mixture of step a) at a temperature ranging from about 20° C. to about 80° C.; and c) stirring the mixture of step b) after adding n-ethyl silicate (TEOS) for a period of time ranging from about 0.5 hour to about 8 hours to obtain the nanoparticle.

BRIEF DESCRIPTION OF THE SEVERAL VIEWS OF THE DRAWING(S)

FIG. 1 illustrates a nanometer-sized particle having a three-layer structure. The black area can be a nanometer-sized magnetic particle or fluorescent particle. The grey area can be a fluorescent material or a magnetic material layer. The shaded area is an outer shell.

FIG. 4 illustrates a 200,000 times transmission electron micrograph (TEM) of fluorescent magnetic particles prepared by the process described in Example 1.

FIG. 5 illustrates an 80,000 times transmission electron micrograph (TEM) of fluorescent magnetic particles prepared by the process described in Example 1.

FIG. 6 illustrates another 80,000 times transmission electron micrograph (TEM) of fluorescent magnetic particles prepared by the process described in Example 1.

FIG. 7 illustrates magnetic hysteresis loop of fluorescent magnetic particles prepared by the process described in Example 1.

DETAILED DESCRIPTION OF THE INVENTION

Figure 1:
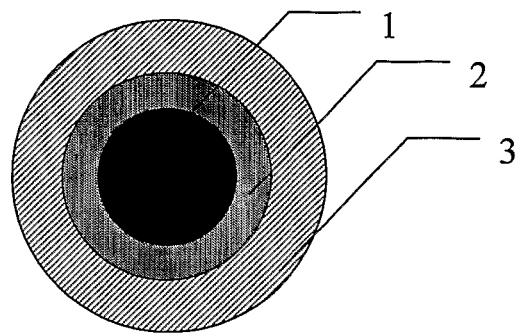

For clarity of disclosure, and not by way of limitation, the detailed description of the invention is divided into the subsections that follow.

A. DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "phosphor" means solid, inorganic, crystalline material that shows luminescence upon optical excitation.

As used herein, "phosphor host" means one (and usually the major one) of the three components in a phosphor which does not participate in the light absorption or light emission process, but provides structural environment for the other two components.

As used herein, "absorber/emitter pair" means the two components in a phosphor which respectively absorbs longer-wavelength light and emits shorter-wavelength light to complete the up-converting process.

B. FLUORESCENT MAGNETIC NANOPARTICLES

The present invention relates to nanometer-sized hybrid fluorescent magnetic particles and processes of making them. The particles are of nanometer-scale and are magnetically-responsive hybrid microspheres that can emit fluorescence when excited by light. The invention can find their utility in a number of fields, including bio-separation and detection.

In one aspect, the present invention provides a nanoparticle comprising a core particle, wherein the core particle comprises a magnetic material and a fluorescent material, and wherein the nanoparticle has a particle size less than about 1 micrometer.

The nanoparticle of the invention may have a size less than about 750 nm, about 500 nm, or about 300 nm. In some embodiments, the particle size ranges from about 35 nm to about 200 nm. In some embodiments, the particle size ranges from about 80 nm to about 200 nm.

Exemplary magnetic material includes a superparamagnetic material, a paramagnetic material, and a ferromagnetic material. In some embodiments, the magnetic material is a metal oxide, such as, oxide of cobalt, nickel, manganese, and iron. In a specific embodiment, the metal oxide is $Fe_3O_4$. In another embodiment, the metal oxide is $\gamma$-$Fe_2O_3$.

In some embodiments, the saturation magnetization of the nanoparticle is between about 5 emu/g to about 60 emu/g.

Exemplary fluorescent material includes a fluorescent dye, a fluorescent organo-metallic compound, an up-converting fluorescent phosphor, a down-converting fluorescent phosphor, and a fluorescent quantum dot. The up-converting fluorescent material can be a phosphor fluoride, such as a phosphor fluoride having a formula of $YF_3$:Yb,Er or $NaYF_4$:Yb,Er. In some embodiments, the up-converting phosphor contains molybdenum. The down-converting phosphor can have a formula of CaS:$Eu^{3+}$ or $SiAlO_2$:$Eu^{3+}$. The fluorescent quantum dot of the inventions can be CdSe/CdS, ZnS/CdSe, or GaAs.

The nanoparticle of the invention can have different configurations for the core particle. For example, the core particle of the invention can comprise a fluorescent nanometer-sized particle covered by a layer of a magnetic material. The fluorescent nanometer-sized particle can be a polymer or silica particle containing a fluorescent material. Alternatively, the core particle can comprise a magnetic particle covered by a layer of a fluorescent material. In another configuration, the core particle can comprise fluorescent particles doped with a magnetic material or magnetic particles doped with the fluorescent material. In another configuration, core particle comprises a magnetic particle, a fluorescent particle, and a material to bind the magnetic particle and the fluorescent particle together. The binding material can be $SiO_2$. In some embodiments, the core particle has a coating layer. For example, the core particle can be coated with $SiO_2$. The thickness of the coating layer may vary, and the size of the nanoparticle and saturation magnetization may depend on the thickness of the coating layer.

In some embodiments, the surface of the nanoparticle can be modified to comprise a functional group. Exemplary functional group includes —COOH, —CHO, —$NH_2$, —SH, —S—S—, an epoxy group, and a trimethoxysilyl group. In some embodiments, the functional group is immobilized on the surface the nanoparticle.

In some embodiments, a bio-molecule may be linked or conjugated to the nanoparticle, covalently or non-covalently. Exemplary bio-molecule includes an amino acid, a peptide, a protein, a nucleoside, a nucleotide, an oligonucleotide, a nucleic acid, a vitamin, a monosaccharide, an oligosaccharide, a carbohydrate, a lipid and a complex thereof. The bio-molecule may be conjugated to the nanoparticle via a chemical functional group or via binding to another biomolecule (such as biotin, streptavidin, and protein A) contained on the surface of the nanoparticle.

The nanoparticle can have any suitable shape, e.g., a rectangle, a circle, an ellipse, or other regular or irregular shapes. Preferably, the nanoparticle has a spherical shape.

C. PROCESSES OF PREPARING FLUORESCENT MAGNETIC NANOPARTICLES

In another aspect, the present invention is directed to a process of preparing a nanoparticle comprising a magnetic particle coated with a phosphor fluoride, which process comprises: a) dispersing a nanometer-sized magnetic particle and an aqueous fluoride-containing compound in de-ionized water; b) contacting the mixture of step a) with an aqueous solution containing soluble salts of a phosphor host, an absorber/emitter pair, and a rare-earth metal chelator by stirring for a sufficient time to allow formation of a phosphor fluoride precipitate which forms a coating around the magnetic particle; and c) heating the magnetic particle with the phosphor fluoride coating of step b) at a temperature ranging from about 300° C. to about 450° C. for a period of time ranging from about 1 hour to about 10 hours to obtain the phosphor fluoride coated magnetic particle that emits light in the visible wavelength range when excited by long wavelength light.

The nanometer-sized magnetic particle and the aqueous fluoride-containing compound can be dispersed in the de-ionized water by any suitable methods, e.g., sonication.

The present process can further comprise coating the phosphor fluoride coated magnetic particle of step c) with a coating layer, e.g., a $SiO_2$ layer. The surface of the nanoparticle can be further modified to comprise a functional group. Exemplary functional group includes —COOH, —CHO, —NH2, —SH, —S—S—, an epoxy group, and a trimethoxysilyl group.

The present process can further comprise immobilizing any desirable moieties, e.g., biological molecules, to the phosphor fluoride particle. For example, the present process can further comprise immobilizing a biological molecule to the $SiO_2$-protected particle. Any suitable biological molecule can be used. Exemplary biological molecules include an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

Any suitable phosphor host can be used in the present processes. For example, yttrium, lanthanum or gadolinium can be used as the phosphor host in the present processes. Any suitable absorber can be used in the present processes. For example, ytterbium can be used as the absorber in the present processes. Any suitable emitter can be used in the present processes. For example, erbium, holmium, terbium or thulium can be used as the emitter in the present processes. In a specific embodiment, the absorber is ytterbium and the emitter is erbium, holmium, terbium or thulium.

Any suitable rare-earth metal chelator can be used in the present processes. For example, ethylenediamineteraacetic acid, triethylenetetraaminhexaacetic acid, diethylenetriaminepentaacetic acid, hydroxyethylethylenediaminetriacetic acid, 1,2-diaminocyclohexanetetraacetic acid, ethylene glycol bis (b-aminoethylether) tetraacetic acid and a salt thereof can be used as the rare-earth metal chelator in the present processes.

Any suitable aqueous fluoride-containing compound can be used in the present processes. For example, NaF, KF, $NH_4F$ and HF can be used as the aqueous fluoride-containing compound in the present processes. The aqueous fluoride-containing compound can be contained in an aqueous solution prior to or concurrently with contacting with the prepared aqueous solution of soluble salts of the phosphor host, the absorber/emitter pair and the rare-earth metal chelator. The amount of the rare-earth metal chelator and the amount of total rare-earth ions in the aqueous solution can have any suitable ratios. For example, the amount of the rare-earth metal chelator can be about 0-1 times the amount of total rare-earth ions in the aqueous solution.

The soluble salts of the phosphor host and the absorber/emitter pair can be prepared by any suitable methods. For example, the soluble salts of the phosphor host and the absorber/emitter pair can be obtained by dissolving the corresponding metal oxide in hydrochloric acid or nitric acid and subsequently removing the residual acid.

In another aspect, the present invention is directed to a process of preparing a nanoparticle comprising fluorescent particles and magnetic particles coated with silica, which process comprises: a) dispersing nanometer-sized magnetic particles and nanometer-sized fluorescent particles in an alcohol; b) adding de-ionized water and ammonia having a concentration of about 28% (w/w) to the mixture of step a) at a temperature ranging from about 20° C. to about 80° C.; and c) stirring the mixture of step b) after adding n-ethyl silicate (TEOS) for a period of time ranging from about 0.5 hour to about 8 hours to obtain the nanoparticle.

Any nanometer-sized magnetic particles can be used for the present process. Exemplary magnetic particles includes superparamagnetic, paramagnetic, and ferromagnetic nanometer-sized particles, and nanometer-sized magnetic oxide of cobalt, nickel, and manganese.

The fluorescent particles of the invention can have a formula of $YF_3$:Yb,Er. The fluorescent particles can also have a formula of NaYF4:Yb,Er. The fluorescent particle can be a fluorescein-doped silica particle.

The surface of the nanoparticle can be modified to contain a functional group. Exemplary functional group includes —COOH, —CHO, —$NH_2$, —SH, —S—S—, an epoxy group, and a trimethoxysilyl group.

The present process can further comprise immobilizing any desirable moieties, e.g., biological molecules, to the phosphor fluoride particle. For example, the present process can further comprise immobilizing a biological molecule to the $SiO_2$-protected particle. Any suitable biological molecule can be used. Exemplary biological molecules include an amino acid, a peptide, a protein, a nucleoside, a nucleotide, an oligonucleotide, a nucleic acid, a vitamin; a monosaccharide, an oligosaccharide, a carbohydrate, a lipid and a complex thereof.

In some embodiments, the alcohol used in the process is 3-propanol.

In other embodiments, the nanometer-sized magnetic particles and the nanometer-sized fluorescent particles are dispersed in the alcohol by sonication for a period of time ranging from about 0.5 hour to about 1 hour.

D. EXEMPLARY EMBODIMENTS

The present invention relates to nanometer-sized hybrid fluorescent magnetic particles and processes of making them. Some embodiments of the nanoparticles of the invention and the processes of making them are described in more detail below and in the Examples.

In some embodiments, the nanoparticles of the invention have a three-layer structure shown in FIG. 1. The black area in the figure is a nanometer-sized magnetic particle. The grey area in the figure is a fluorescent material layer with nanometer-thickness, such as inorganic, organic, or polymer fluorescent materials. The outer shell can be inorganic materials such as silica, or polymeric organic compounds.

Alternatively, the black area is a nanometer-sized fluorescent particle, including inorganic, organic or polymer fluorescent particles. The grey area is a magnetic material layer with nanometer-thickness. The magnetic material can be a hybrid material made of magnetic materials and polymer or some other materials. The outer shell can be inorganic materials such as silica, or polymeric organic compounds.

The magnetic materials can be superparamagnetic, paramagnetic or ferromagnetic nanometer-sized particles or other nanometer-sized magnetic oxide of iron, cobalt, nickel or manganese etc.

The fluorescent materials can be up-converting fluorescent materials for example, phosphor fluoride nanoparticles (Yi Guangshun et al, CN: 02116679.X), molybdenum up-converting phosphor particles (Yi Guangshun et al, CN 01134861.5), etc.; nanometer-sized down-converting rare-earth materials, for example, CaS:Eu3+, SiAlO2:Eu3+, etc; fluorescent quantum dots, for example, CdSe/CdS, ZnS/CdSe, GaAs, etc.; and fluorescent nanometer-sized particles, for example, polymer nanometer-sized particles containing fluorescent materials (Taylor J R et al Anal. Chem., 2000, 72: 1979-1986) and luminophore-doped silica nanoparticles (Santra S et al, Anal. Chem., 2001, 73: 4988~4993), etc.

Referring to Yi's patent (CN: 02116679X), a type of three-layer up-converting fluorescent magnetic nanoparticles can be prepared in the following way. Nanometer-sized magnetic particles and an aqueous fluoride-containing compound is dispersed in de-ionized water by sonication. An aqueous solution of soluble salts of a phosphor host, an absorber/emitter pair and a rare-earth metal chelator are added into the solution. After vigorous stirring for sufficient time the precipitate of phosphor fluoride is formed as a coating around the magnetic particles. The two-layer structure is formed. Then the particles with a precipitate of phosphor fluoride layer are heated at a temperature ranging from about 300° C. to 450° C. for a period of time ranging from about 1 hour to about 10 hours to obtain two-layer magnetic particles with shells of phosphor fluoride materials that emit light in the visible wavelength range when excited by infrared ray. These uniform particles have a size of less than 150 nm. A three-layer structure might be formed bicoating a silica layer or polymer layer around the two-layer fluorescent magnetic particle. Furthermore these three-layer particles might be surface-modified with different groups. The particles have a size less than 300 nm. Process is further described in detail in Example 8.

These fluorescent magnetic particles having surface modification with amino group, epoxy group, trimethoxysilyl group, sulfhydryl group and other functional groups can be obtained by reacting with 3-aminopropy-trimethoxyklne (APS), 3-glycidoxypropyl-trimethoxysilane (GPMS), g-methacryloxypropyltrimethoxy-silane (MPS), 3-mercaptopropyltrimethoxysilane (MPTS) and other functional silane reagents respectively. The epoxy-modified particles can be then treated sequentially with 0.01 mol/L hydrochloric acid and 0.2 mol/L sodium periodate solution to obtain aldehyde modified particles.

Figure 2:
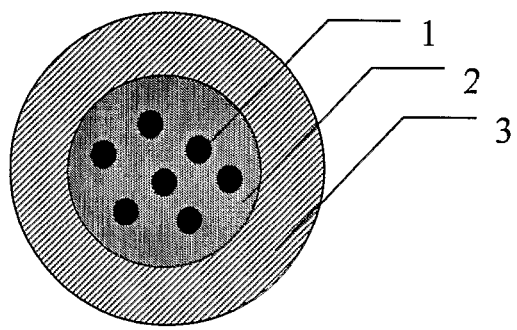
FIG. 2 illustrates a nanometer-sized particle having a core composed of magnetic material and fluorescent material and a shell (shaded). The core can be a fluorescent material (black) doped with a magnetic material (grey) or a magnetic material (black) doped with a fluorescent material (grey).

In some embodiments, the nanoparticle of the invention is a nanometer-scaled sphere with a core-shell structure (FIG. 2), in which the core has uniform composition composed of magnetic and fluorescent materials. The shell is a protective coating of inorganic or polymeric material with surface active functionalities.

The core can be a fluorescent material doped with a magnetic material or a magnetic material doped with a fluorescent material.

The magnetic materials can be superparamagnetic, paramagnetic, ferromagnetic nanometer-sized materials, or other nanometer-sized magnetic oxide of iron, cobalt, nickel or manganese.

The fluorescent materials can be up-converting fluorescent materials for example, phosphor fluoride nanoparticles (Yi Guangshun et al, CN: 02116679.X), molybdenum up-converting phosphor particles (Yi Guangshun et al, CN 01134861.5); nanometer-sized down-converting rare-earth materials, for example, CaS:Eu3+, SiAlO2:Eu3+; fluorescent quantum dots, for example, CdSe/Cd, ZnS/CdSe, GaAs; and fluorescent nanometer-sized particles, for example, polymer nanometer-sized particles containing fluorescent materials (Taylor J R et al Anal. Chem., 2000, 72: 1979-1986) and luminophore-doped silica nanoparticles (Santra S et al, Anal. Chem., 2001, 73: 4988~4993).

These fluorescent magnetic particles having surface modification with amino group, epoxy group, trimethoxysilyl group, thiohydroxy group and other functional groups can be obtained by reacting with 3-aminopropy-trimethoxysilne (APS), 3-glycidoxypropyl-trimethoxysilane (GPMS), g-methacryloxypropyltrimethoxy-silane (MPS), 3-mercaptopropyltrimethoxysilane (MPTS) and other functional silane reagents respectively. The epoxy-modified particles can be then treated sequentially with 0.01 mol/L hydrochloric acid and with 0.2 mol/L sodium periodate solution to obtain aldehyde modified particles.

Figure 3:
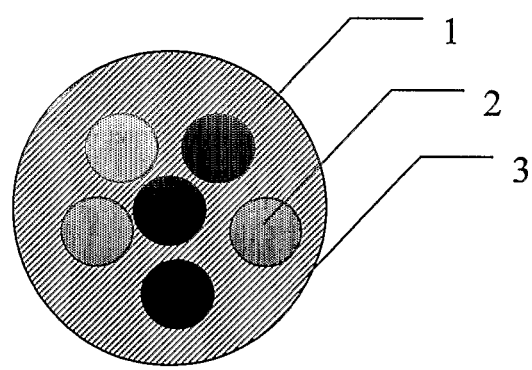
FIG. 3 illustrates a nanometer-sized particle comprising a fluorescent nanosphere (black), a magnetic nanosphere (grey), and a material (shaded) to bind them together.
Figure 8:
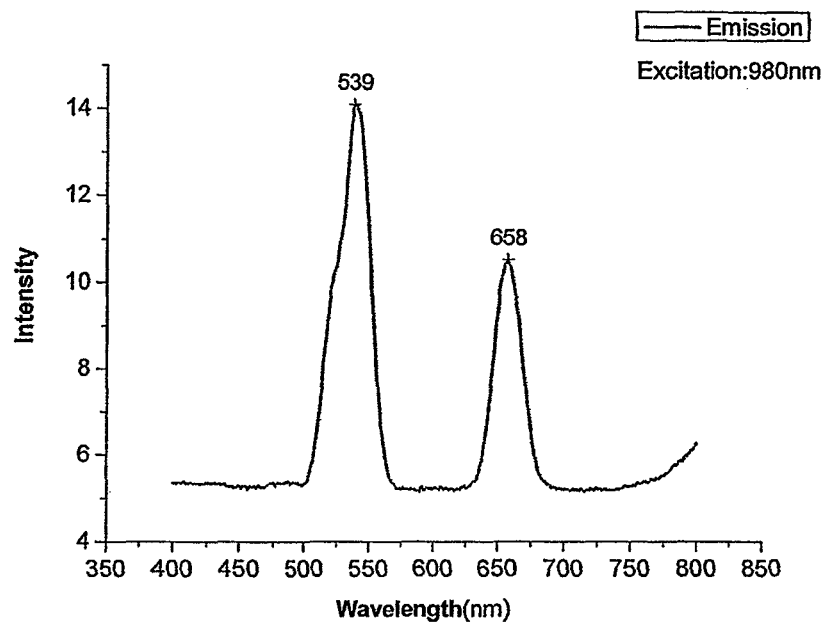
FIG. 8 illustrates emission curve of up-converting fluorescence (excited at 980 nm) of fluorescent magnetic particles prepared by the process described in Example 1.
Figure 9:
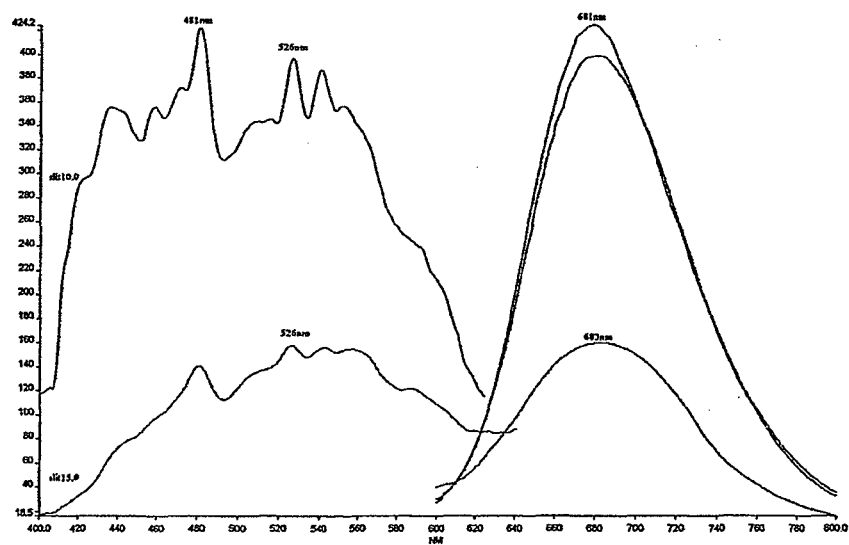
FIG. 9 illustrates emission curve of down-converting fluorescence of Casein$^+$ fluorescent magnetic particles prepared by the process described in Example 2.
Figure 10:
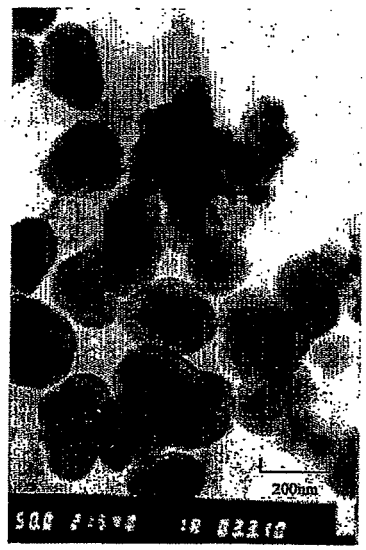
FIG. 10 illustrates a 50,000 times transmission electron micrograph (TEM) of three-layer fluorescent magnetic particles prepared by the process described in Example 8.
Figure 11:
FIG. 11 illustrates a 100,000 times transmission electron micrograph (TEM) of three-layer fluorescent magnetic particles prepared by the process described in Example 8.
Figure 12:
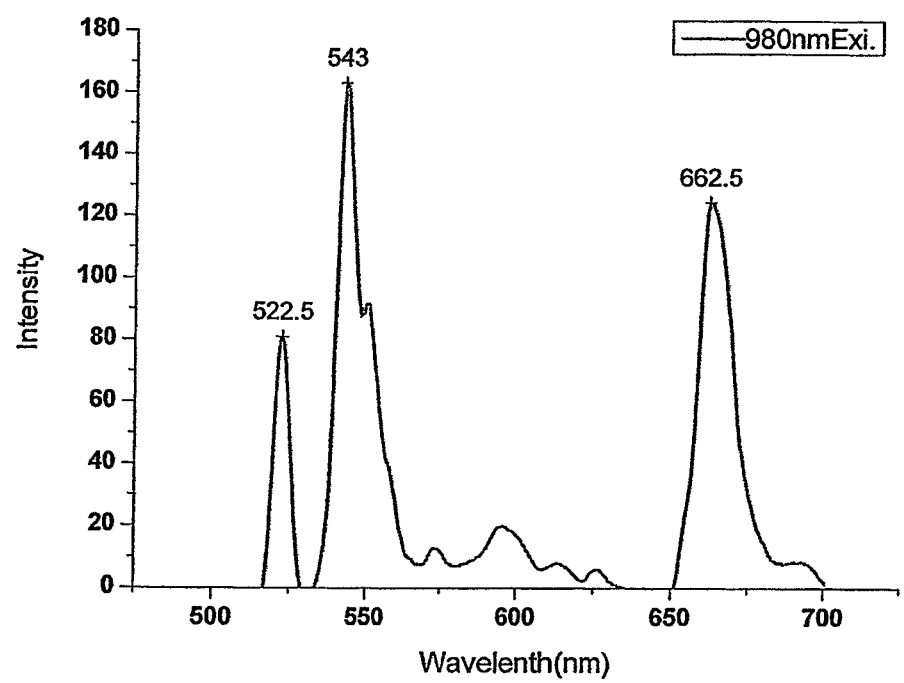
FIG. 12 illustrates emission curve of up-converting fluorescence (excited at 980 nm) of three-layer fluorescent magnetic particles prepared by the process described in Example 8.
Figure 13:
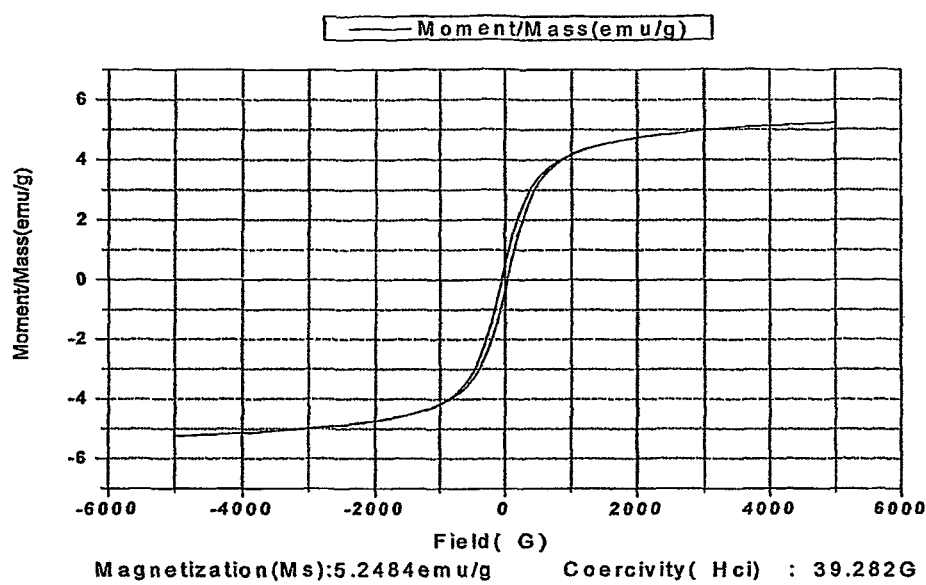
FIG. 13 illustrates magnetic hysteresis loop of three-layer fluorescent magnetic particles prepared by the process described in Example 8.

In other embodiments, the nanoparticle of the invention comprises a fluorescent nanosphere, a magnetic nanosphere and a material to bind them together (FIG. 3).

Nanometer-sized magnetic particles and fluorescent nanoparticles can be dispersed in 3-propanol by sonication for a period of time ranging from about 0.5 hour to about 1 hour. De-ionized water and 28% ammonia ($NH_3 \cdot H_2O$) are added at a temperature ranging from about 20° C. to 80° C. Then, n-Ethyl silicate (TEOS) is added and the mixture is stirred for a period of time ranging from about 0.5 hour to 8 hours. The fluorescent magnetic particles coated with silica are obtained.

To obtain surface-modified nanoparticles, various silanes can be added into the reaction mixture described above and allowed to react for a period of time. The nanoparticles are separated with a magnetic concentrator (commercially acquired from ProMega Co.) and washed with 3-propanol, distilled water and ethanol. The nanoparticles are then dried at temperature from 40° C. to 110° C. Nanoparticles having surface modification with various of groups are obtained.

The magnetic materials can be superparamagnetic, paramagnetic or ferromagnetic nanometer-sized particles or other nanometer-sized magnetic oxide of iron, cobalt, nickel or manganese etc.

The fluorescent materials include up-converting fluorescent materials for example, phosphor fluoride nanoparticles (Yi Guangshun et al, CN: 02116679.X), molybdenum up-converting phosphor particles (Yi Guangshun et al, CN 01134861.5); nanometer-sized down-converting rare-earth materials, for example, $CaS:Eu^{3+}$, $SiAlO2:Eu^{3+}$; fluorescent quantum dots, for example, CdSe/CdS, ZnS/CdSe, GaAs; and fluorescent nanometer-sized particles, for example, polymer nanometer-sized particles containing fluorescent materials (Taylor J R et al Anal. Chem., 2000, 72: 1979-1986) and luminophore-doped silica nanoparticles (Santra S et al, Anal. Chem., 2001, 73: 4988~4993).

The material which binds fluorescent materials and magnetic materials together can also be polymeric organic compounds besides silica described above.

Fluorescent magnetic nanoparticles having surface-modification with amino group, epoxy group, trimethoxysilyl group, sulfhydryl group and other functional groups can be obtained by reacting with 3-aminopropy-trimethoxysilne (APS), 3-glycidoxypropyl-trimethoxysilane (GPMS), g-methacryloxypropyltrimethoxy-silane (MPS), 3-mercaptopropyltrimethoxysilane (MPTS) and other functional silane reagents respectively. The epoxy-modified particles can be then treated sequentially with 0.01 mol/L hydrochloric acid and with 0.2 mol/L sodium periodate solution to obtain aldehyde modified particles.

The nanometer-sized fluorescent magnetic particles prepared in the process described above may have the following characteristics:

1) The particle size is on the nanometer scale and can range from about 50 nm to about 200 nm. The particle size depends on the size of cores and the thickness of the coating layer.
2) The particles can have saturation magnetization ranging from about 5 emu/g to about 60 emu/g. The saturation magnetization can vary with the thickness of the coating layer. The particles can have a very low coercivity (for example, less then 20G). All these features meet the requirement for bio-separation.
3) The particles which embed inorganic nanometer-sized fluorescent material such as quantum dots or up-converting fluorescent materials have better fluorescent characteristic, larger Stokes shift, lower background and greater signal-noise ratio than using fluorescent dyes.
4) The particles can be coated with amino group, epoxy group, aldehyde group, or other function groups which can be used to link proteins, nucleic acid, and other biomolecules to the surface of the particles.
5) These nanoparticles can be used both as solid phase carrier in separation and fluorescent labels for various types of immunoassay, DNA/RNA hybridization and detection, affinity purification, cell separation and other medical, diagnostic, and industrial applications.

E. EXAMPLES

Example 1

Preparation of Fluorescent Magnetic Nanoparticles

1) To prepare nanometer-sized magnetic particles, 1.622 g of ferric chloride ($FeCl_3$) and 5.560 g of ferrous sulfate ($FeSO_4 \cdot 7H_2O$) were dissolved in 200 ml of de-ionized water which had been de-oxygenized with nitrogen bubble overnight. The concentration of ferric ion ($[Fe^{3+}]$) was 0.05 mol/L and the concentration of ferrous ion ($[Fe^{2+}]$) was 0.10 mol/L. 1.0 g of polyglycol-4000 was added in the mixture and dispersed by sonication for 30 minutes. The mixture was stirred rapidly at a temperature of 60° C. Then 10 ml of 28% ammonia was added into the mixture rapidly. The mixture was stirred rapidly for 30 minutes with nitrogen atmosphere all the time. The superparamagnetic particles was isolated with a magnetic concentrator and washed several times with de-ionized water and alcohol. The particles were dried in vacuum at a temperature of 60° C. overnight. Dark brown nanometer-sized magnetic particles were obtained after pestling.
2) 15 mg of magnetic particles prepared in step 1) and 15 mg of YF3:Yb,Er prepared according to CN:02116679.X were dispersed in 100 ml of 3-propanol by sonication for more than 30 minutes so that two types of particles were well-distributed in the solution. 8.94 ml of 28% ammonia was then added into the mixture as a catalyzer and 7.5 ml of de-ionized water was added as a hydrolytic reagent. The mixture was heated at temperature of 40° C. in the oil bath. Then, 0.2 ml of n-ethyl silicate (TEOS) was added into the mixture and after stirred for 3 hours. The particles were isolated with a magnetic concentrator and washed several times with 3-propanol, de-ionized water and alcohol. The fluorescent magnetic particles prepared were dried in vacuum at a temperature of 110° C. for 6 hours.

Example 2

Preparation of Magnetic Particles with Red Fluorescence

1) To prepare magnetic nanoparticles with red fluorescence, 30 mg of magnetic particles prepared in example 1 and 30 mg of nanometer-sized rare-earth particles $CaS:Eu^{3+}$ were dispersed in 80 ml of 3-propanol by sonication for more than 30 minutes. The mixture turned to be well-distributed solution after enough sonication. 8.94 ml of 28% ammonia was added into the mixture as a catalyzer and 7.5 ml of de-ionized water was added as a hydrolytic reagent. The mixture was heated at temperature of 40° C. in the oil bath. Then, 0.15 ml of n-ethyl silicate (TEOS) was added into the mixture and the reaction was stopped after stirring for about 3 hours.
2) Then the particles were isolated with a magnetic concentrator and washed several times with 3-propanol, de-ionized water, and alcohol. Then the particles were dried in vacuum at a temperature of 60° C. for 5 hours. The magnetic particles with red fluorescence were obtained.

Example 3

Preparation of Fluorescent Magnetic Nanoparticles with Amino Groups on the Surface 1) To obtain fluorescent magnetic nanoparticles with amino groups on the surface, 30 mg of magnetic particles prepared in Example 1 and 20 mg of YF3: Yb,Er prepared according to CN:02116679.X were dispersed in 80 ml of 3-propanol by sonication for more than 30 minutes so that the particles were well-distributed in the solution. 8.94 ml of 28% ammonia was added into the mixture as a catalyzer and 7.5 ml of de-ionized water was added as a hydrolytic reagent. The mixture is heated at temperature of 40° C. in the oil bath. Then, 0.1 ml of n-ethyl silicate (TEOS) was added into the mixture and the mixture was stirred for about 2 hours. Then, 0.1 ml of 3-aminopropy-trimethoxysilne (APS) was added into the mixture. The reaction continued for one additional hour.

2) Then the particles were isolated with a magnetic concentrator and washed several times with 3-propanol, de-ionized water and alcohol. The fluorescent magnetic particles were then dried in vacuum at a temperature of 50° C. for 6 hours. Fluorescent magnetic nanoparticles with amino groups on the surface were obtained.

Example 4

Preparation of Fluorescent Magnetic Nanoparticles with Aldehyde Groups on the Surface 1) To obtain fluorescent magnetic nanoparticles with aldehyde groups on the surface, 30 mg of magnetic particles prepared in Example 1 and 30 mg of YF3:Yb,Er prepared according to CN:02116679.X were dispersed in 160 ml of 3-propanol by sonication for 30 to 40 minutes so that the particles were well-distributed in the solution. 17.8 ml of 28% ammonia aqueous was added into the mixture as a catalyzer and 15.0 ml of de-ionized water was added as a hydrolytic reagent. The mixture was heated at temperature of 40° C. in the oil bath. 0.1 ml of n-ethyl silicate (TEOS) was then added into the mixture. After being stirred for about 2 hours, the reaction was stopped.

2) Then the particles were isolated with a magnetic concentrator and washed several times with 3-propanol, de-ionized water, and alcohol. After being washed with acetone. 3 ml toluene solution with 10% 3-glycidoxypropyl-trimethoxysilane(GPMS) was mixed with the particles and the reaction was carried out on the shaking table overnight. Then the particles were isolated with a magnetic concentrator and washed several times with toluene and acetone. Then the particles were dried in vacuum at a temperature of 110° C. for 2 hours.

3) The dried particles were acidified with 4 ml of 0.01 mol/L hydrochloric acid and the mixture was stirred on a shaking table for 0.5 hour. Then the particles were washed with de-ionized water several times. The particles were oxidized with 4 ml sodium periodate solution at a concentration of 0.2 mol/L for 1 hour. Then the particles were isolated with a magnetic concentrator and washed with de-ionized water. The particles were dried in vacuum at a temperature of 60° C. for 6 hours. The fluorescent magnetic nanoparticles with aldehyde groups on the surface were obtained.

Example 5

Preparation of Fluorescent Magnetic Nanoparticles with Epoxy Groups on the Surface 1) To obtain fluorescent magnetic nanoparticles with epoxy groups on the surface, 30 mg of magnetic particles prepared in Example 1 and 30 mg of YF3:Yb,Er prepared according to CN:02116679.X were dispersed in 160 ml of 3-propanol by sonication for more than 30 minutes so that the particles were well-distributed in the solution. 17.8 ml of 28% ammonia was added into the mixture as a catalyzer and 15.0 ml of de-ionized water was added as a hydrolytic reagent. The mixture was heated at temperature of 40° C. in the oil bath. 0.1 ml of n-ethyl silicate (TEOS) was added into the mixture. After stirring for about 2 hours, 0.1 ml of 3-glycidoxypropyl-trimethoxysilane(GPMS) was added into the mixture. The reaction continued for one additional hour and then was stopped.

2) Then the particles were isolated with a magnetic concentrator and washed several times with 3-propanol, de-ionized water, and alcohol. Then the fluorescent magnetic particles were dried in a vacuum at a temperature of 60° C. for 6 hours. The fluorescent magnetic particles with epoxy groups on the surface were obtained.

Example 6

Preparation of Fluorescent Magnetic Nanoparticles with a Thin Coating Layer

1) To obtain fluorescent magnetic nanoparticles with a thin coating layer, 30 mg of magnetic particles prepared in Example 1 and 30 mg of YF3:Yb,Er prepared according to CN:02116679.X were dispersed in 160 ml of 3-propanol by sonication for more than 30 minutes so that the particles were well-distributed in the solution. 17.8 ml of 28% ammonia aqueous was added into the mixture as a catalyzer and 15.0 ml of de-ionized water was added as a hydrolytic reagent. The mixture was heated at temperature of 40° C. in the oil bath. 0.05 ml of n-ethyl silicate (TEOS) was added into the mixture. After stirring for about 2 hours, the reaction was stopped.

2) Then the particles were isolated with a magnetic concentrator and washed several times with 3-propanol, de-ionized water, and alcohol. The particles were dried in vacuum at a temperature of 60° C. for 6 hours. The fluorescent magnetic nanoparticles with a thin coating layer were obtained.

Example 7

Preparation of Fluorescent Magnetic Nanoparticles with a Thick Coating Layer

1) To obtain fluorescent magnetic nanoparticles with a thick coating layer, 30 mg of magnetic particles prepared in Example 1 and 30 mg of YF3:Yb,Er prepared according to CN:02116679.X were dispersed in 160 ml of 3-propanol by sonication for more than 30 minutes so that the particles were well-distributed in the solution. 17.8 ml of 28% ammonia aqueous was added into the mixture as a catalyzer and 15.0 ml of de-ionized water was added as a hydrolytic reagent. The mixture was heated at temperature of 40° C. in the oil bath. 0.2 ml of n-ethyl silicate (TEOS) was added in the solution during stirring the mixture and the reaction continued for about 2 hours.

2) Then the particles were isolated with a magnetic concentrator and washed several times with 3-propanol, de-ionized water, and alcohol. The particles were dried in a vacuum at a temperature of 60° C. for 6 hours. The fluorescent magnetic nanoparticles with a relatively thick coating layer were obtained.

Example 8

Preparation of Fluorescent Magnetic Nanoparticles Having Three-Layer Structure 1) 100 mg of magnetic particles prepared in Example 1 and 2.1 g of sodium fluoride were dissolved in 120 ml of de-ionized water and a well-distributed colloid solution was prepared by sonication for more than 40 minutes.
2) Stock solutions of $YCl_3$ (0.2 mol/L), $YbCl_3$ (0.2 mol/L) and $ErCl_3$ (0.2 mol/L) were mixed at a volume ratio of 16.0 mL:3.40 mL:0.60 mL in a 100 mL beaker. The molar ratio of lanthanide ions in the mixture was $Y^{3+}:Yb^{3+}:Er^{3+}=80:17:3$.
3) 20 mL of 0.2 M EDTA solution was introduced into the solution prepared in 2). Then the mixture solution was introduced into the solution prepared in 1) with rapidly stirring for 1 hour.
4) The magnetic particles were isolated with a magnetic concentrator and the nonmagnetic particles were washed away with de-ionized water until the cleaning solution was clear. Then the magnetic particles were heated in muffle furnace for 5 hr with hydrogen atmosphere all the time. And magnetic particles having a two-layer structure were obtained.
5) 30 mg of particles prepared in 4) were dispersed in 80 ml of 3-propanol by sonication for more than 30 minutes so that the particles were well-distributed in the solution. 8.94 ml of 28% ammonia aqueous was added into the mixture as a catalyzer and 7.5 ml of de-ionized water was added as a hydrolytic reagent. The mixture was heated at temperature of 40° C. in the oil bath. 0.1 ml of n-ethyl silicate (TEOS) was added into the mixture. After being stirred for about 3 hours, the reaction was stopped.
6) Then the particles were isolated with a magnetic concentrator and washed several times with 3-propanol, de ionized water and alcohol. The particles were dried in a vacuum at a temperature of 110° C. for 6 hours. The fluorescent magnetic nanoparticles with a three-layer structure having a size ranging from about 80 to about 200 nm were obtained.

Example 9

Preparation of FITC Fluorescent Magnetic Particles with Aldehyde Groups on the Surface 1) 30 mg of magnetic particles prepared in Example 1 and 20 mg of FITC-doped silica nanoparticles were dispersed in 160 ml of 3-propanol by sonication for more than 30 minutes so that the particles were well-distributed in the solution. 17.8 ml of 28% ammonia aqueous was added into the mixture as a catalyzer and 15.0 ml of de-ionized water was added as a hydrolytic reagent. The mixture was heated at temperature of 40° C. in the oil bath. 0.1 ml of n-ethyl silicate (TEOS) was added in the solution. After being stirred for about 2 hours, 0.1 ml of 3-glycidoxypropyl-trimethoxysilane(GPMS) was added into the mixture. The reaction was allowed to continue for one additional hour and was stopped.
2) Then the particles were isolated with a magnetic concentrator and washed several times with 3-propanol, de-ionized water, and alcohol. Then the particles were dried in a vacuum at a temperature of 60° C. for 6 hours. The FITC fluorescent magnetic nanoparticles with epoxy group on the surface were obtained.
3) The dried particles were acidified with 4 ml hydrochloric acid with a concentration of 0.01 mol/L and the mixture was stirred on a shaking table for 0.5 hour. Then the particles were washed with de-ionized water several times. The particles were oxidized with 4 ml sodium periodate solution at a concentration of 0.2 mol/L for 1 hour. Then the particles were isolated with a magnetic concentrator and washed with de-ionized water. The particles were then dried in a vacuum at a temperature of 60° C. for 6 hours. The FITC fluorescent magnetic nanoparticles with aldehyde groups on the surface were obtained.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The invention claimed is:

1. A nanoparticle comprising a core particle and an outer shell, wherein the core particle comprises a magnetic particle, a fluorescent particle, and a material that binds the magnetic particle and the fluorescent particle together, wherein the fluorescent particle comprises an up-converting phosphor fluoride, wherein the core particle is coated with the outer shell, and wherein the size of the nanoparticle is less than about 1 micrometer.

2. The nanoparticle of claim 1, wherein the size of the nanoparticle is less than about 300 nanometers.

3. The nanoparticle of claim 1, wherein the size of the nanoparticle is ranging from about 80 nanometers to about 200 nanometers.

4. The nanoparticle of claim 1, wherein the magnetic particle comprises a superparamagnetic, a paramagnetic or a ferromagnetic material.

5. The nanoparticle of claim 1, wherein the magnetic particle comprises a metal oxide.

6. The nanoparticle of claim 5, wherein the metal oxide is selected from the group consisting of oxide of cobalt, nickel, manganese, and iron.

7. The nanoparticle of claim 1, wherein the saturation magnetization of the nanoparticle is between about 5 emu/g and about 60 emu/g.

8. The nanoparticle of claim 1, wherein the fluorescent particle is a fluorescent nanometer-sized particle.

9. The nanoparticle of claim 1, wherein the core particle comprises a magnetic particle covered by a layer of the fluorescent particle.

10. The nanoparticle of claim 1, wherein the core particle comprises a fluorescent particle covered by a layer of the magnetic material.

11. The nanoparticle of claim 1, wherein the core particle comprises fluorescent particles doped with the magnetic material.

12. The nanoparticle of claim 1, wherein the core particle comprises magnetic particles doped with the fluorescent material.

13. The nanoparticle of claim 1, which comprises a bio-molecule.

14. The nanoparticle of claim 13, wherein the bio-molecule is selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

15. The nanoparticle of claim 1, wherein the material that binds the magnetic particle and the fluorescent particle together comprises $SiO_2$ or a polymeric organic compound.

16. The nanoparticle of claim 1, wherein the outer shell comprises silica or a polymeric organic compound.

17. The nanoparticle of claim 1, wherein the fluorescent particle is a fluorescein-doped silica particle.

18. The nanoparticle of claim 1, wherein the surface of the nanoparticle comprises a functional group.

19. The nanoparticle of claim 18, wherein the functional group is selected from the group consisting of —COOH, —CHO, —NH$_2$, —SH, —S—S—, a sulfhydryl group, an epoxy group, and a trimethoxysilyl group.

* * * * *